United States Patent
Quallich et al.

(10) Patent No.: US 6,794,388 B2
(45) Date of Patent: Sep. 21, 2004

(54) SUCCINIC ACID SALTS OF 5,7,14-TRIAZATETRACYCLO [10.3.1.0$^{2,11}$.0$^{4,9}$] -HEXADECA-1(11),3,5, 7,9-PENTAENE AND PHARMACEUTICAL COMPOSITIONS THEREOF

(75) Inventors: George J. Quallich, North Stonington, CT (US); Lewin T. Wint, Wilmette, IL (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/305,845

(22) Filed: Nov. 27, 2002

(65) Prior Publication Data

US 2003/0149044 A1 Aug. 7, 2003

Related U.S. Application Data

(60) Provisional application No. 60/334,245, filed on Nov. 29, 2001.

(51) Int. Cl.$^7$ .................. C07D 471/08; A61K 31/4995
(52) U.S. Cl. ....................................... 514/250; 544/343
(58) Field of Search ............................. 514/250, 214.03; 544/343; 540/578

(56) References Cited

FOREIGN PATENT DOCUMENTS

| WO | WO9935131 | 7/1999 |
|----|-----------|--------|
| WO | 1157726 | 11/2001 |

*Primary Examiner*—Bruck Kifle
(74) *Attorney, Agent, or Firm*—P. C. Richardson; P. H. Ginsburg; A. D. Joran

(57) ABSTRACT

The present invention is directed to the succinate salts of 5,7,13-triazatetracyclo[9.3.1.0$^{2,10}$.0$^{4,8}$]-pentadeca-2(10),3,5,8-tetraene

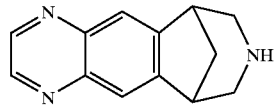

and pharmaceutical compositions thereof. The invention is also directed to a process for preparation of the succinate salts.

18 Claims, 4 Drawing Sheets

SUCCINIC ACID SALTS OF 5,7,14-TRIAZATETRACYCLO [10.3.1.0$^{2,11}$.0$^{4,9}$] -HEXADECA-1(11),3,5, 7,9-PENTAENE AND PHARMACEUTICAL COMPOSITIONS THEREOF

This application claims benefit of Application No. 60/334,245 filed Nov. 29, 2001.

The present invention is directed to the succinate salts of 5,8,14-triazatetracyclo[10.3.1.0$^{2,11}$.0$^{4,9}$]-hexadeca-2(11),3,5,7,9-pentaene

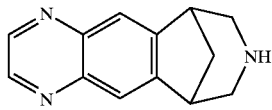

and pharmaceutical compositions thereof. The succinate salts can take an anhydrous form or a hydrated form.

The compound, 5,8,14-triazatetracyclo[10.3.1.0$^{2,11}$.0$^{4,9}$]-hexadeca-2(11),3,5,7,9-pentaene, binds to neuronal nicotinic acetylcholine specific receptor sites and is useful in modulating cholinergic function. This compound is useful in the treatment of inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supramuscular, palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD) and Tourette's Syndrome.

The succinate salts of this invention may also be used in a pharmaceutical composition in combination with an antidepressant such as, for example, a tricyclic antidepressant or a serotonin reuptake inhibiting antidepressant (SRI), in order to treat both the cognitive decline and depression associated with AD, PD, stroke, Huntington's chorea or traumatic brain injury (TBI); in combination with muscarinic agonists in order to stimulate both central muscarinic and nicotinic receptors for the treatment, for example, of ALS, cognitive dysfunction, age-related cognitive decline, AD, PD, stroke, Huntington's chorea and TBI; in combination with neurotrophic factors such as NGF in order to maximize cholinergic enhancement for the treatment, for example, of ALS, cognitive dysfunction, age-related cognitive decline, AD, PD stroke, Huntington's chorea and TBI; or in combination with agents that slow or arrest AD such as cognition enhancers, amyloid aggregation inhibitors, secretase inhibitors, tau kinase inhibitors, neuronal anti-inflammatory agents and estrogen-like therapy.

Compounds that bind to neuronal nicotinic receptor sites, including 5,8,14-triazatetracyclo[10.3.1.0$^{2,11}$.0$^{4,9}$]-hexadeca-2(11),3,5,7,9-pentaene, and its hydrochloride salt, are referred to in WO 99/35131, published Jul. 15, 1999 (corresponding to U.S. Ser. Nos. 09/402,010, filed Sep. 28, 1999 and 09/514,002, filed Feb. 25, 2000). The foregoing applications, owned in common with the present application and incorporated herein by reference in their entirety, generically recite pharmaceutically acceptable acid addition salts for the compounds referred to therein.

The succinate salts of the present invention exhibits properties, including those of solid-state stability and compatibility with certain drug product formulation excipients, that render it preferable among known salts of 5,8,14-triazatetracyclo[10.3.1.0$^{2,11}$.0$^{4,9}$]-hexadeca-2(11),3,5,7,9-pentaene. Further, the succinate salt formation is an extremely efficient means of purifying 5,8,14-triazatetracyclo[10.3.1.0$^{2,11}$ .0$^{4,9}$]-hexadeca-2(11),3,5,7,9-pentaene.

SUMMARY OF THE INVENTION

Figure 1:
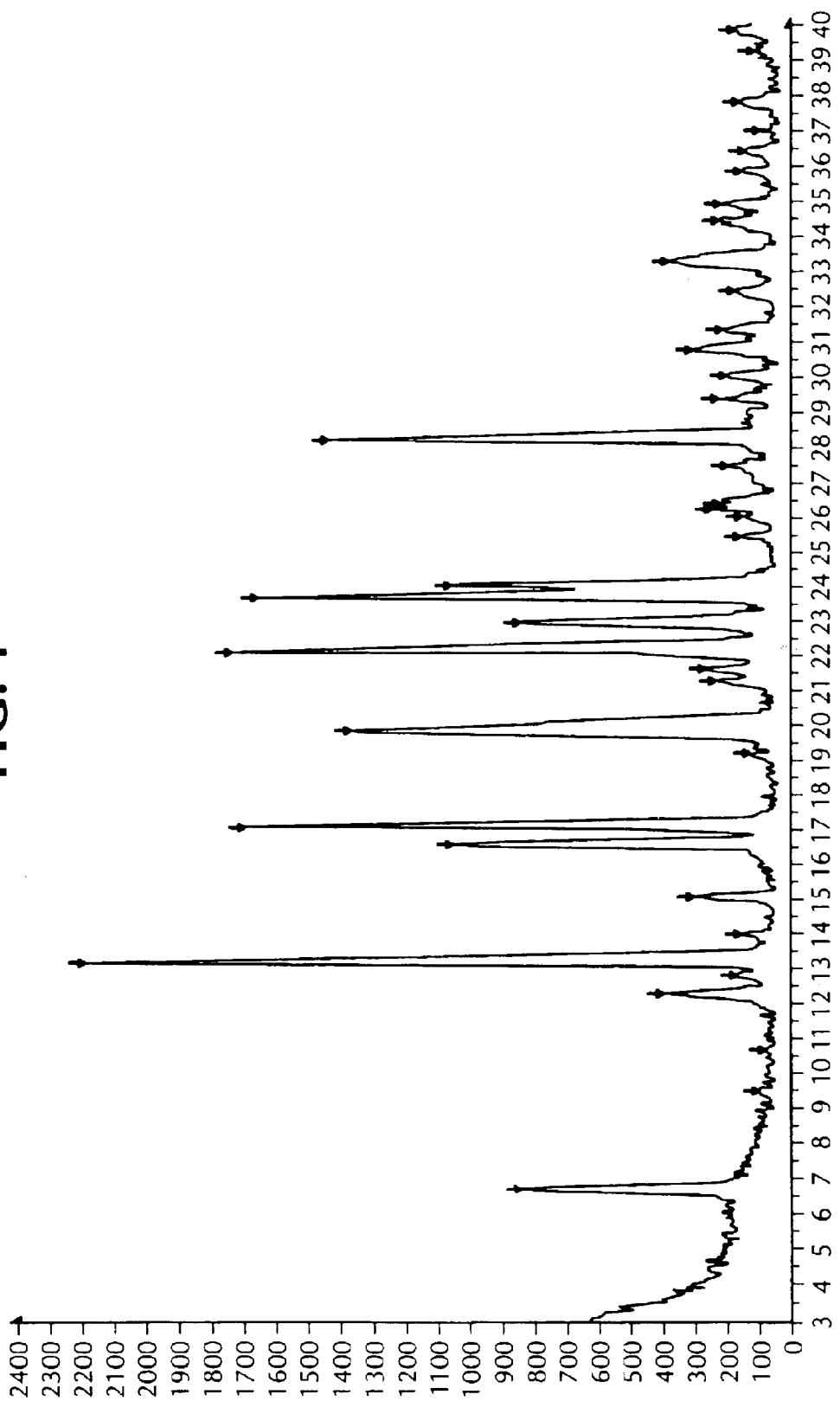
FIG. 1 is the observed powder X-ray diffraction pattern of the anhydrous succinate salt of 5,8,14-triazatetracyclo [10.3.1.0$^{2,11}$.0$^{4,9}$]-hexadeca-2(11),3,5,7,9-pentaene (y axis is linear counts per second; X in degrees 2 theta).

The present invention relates to the succinate salt of 5,8,14-triazatetracyclo[10.3.1.0$^{2,11}$.0$^{4,9}$]-hexadeca-2(11),3,5,7,9-pentaene. In particular, the present invention relates to the anhydrous and hydrate forms of this succinate salt. Particularly preferred is the anhydrous succinate salt.

Another embodiment of the invention relates to a pharmaceutical composition comprising the succinate salt of 5,8,14-triazatetracyclo[10.3.1.0$^{2,11}$.0$^{4,9}$]-hexadeca-2(11),3,5,7,9-pentaene and a pharmaceutically acceptable carrier or excipient, particularly, one for use in the treatment of inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supramuscular palsy, chemical dependencies and addictions (eq., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD) and Tourette's Syndrome. Another more preferred embodiment of the invention is wherein the pharmaceutical composition above is useful in the treatment of nicotine dependency, addiction and withdrawal, most preferably, for use in smoking cessation therapy.

The present invention further relates to a the method of treating inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supramuscular palsy, chemical dependencies and addictions (e.q., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD) and Tourette's Syndrome comprises administering to a subject in need of treatment a therapeutically effective amount of the succinate salt of 5,8,14-triazatetracyclo[$10.3.1.0^{2,11}.0^{4,9}$]-hexadeca-2(11),3,5,7,9-pentaene thereof. Another more preferred embodiment of the invention relates to a method of treatment for nicotine dependency, addiction and withdrawal, in particular for use in smoking cessation therapy activity, comprising the administration of the succinate salt of 5,8,14-triazatetracyclo [$10.3.1.0^{2,11}.0^{4,9}$]-hexadeca-2(11),3,5,7,9-pentaene to a subject in need thereof.

The invention also relates to a process for the preparation of the anhydrous succinate salt of 5,8,14-triazatetracyclo [$10.3.1.0^{2,11}.0^{4,9}$]-hexadeca-2(11),3,5,7,9-pentaene comprising the steps of (i) contacting 5,8,14-triazatetracyclo[$10.3.1.0^{2,11}.0^{4,9}$]-hexadeca-2(11),3,5,7,9-pentaene in a suitable solvent with succinic acid; and (ii) collecting the crystals formed.

A preferred embodiment is wherein the suitable solvent is selected from the group consisting of a ($C_1$–$C_6$)alkyl alcohol, a ($C_1$–$C_6$)alkyl ketone or a ($C_1$–$C_6$)alkyl ether in the presence of water. More preferably, the suitable solvent is acetone or 2-propanol. Most preferably, the suitable solvent is 2-propanol. Preferably, the process of the invention is wherein the contacting of step (i) is carried out by contacting 5,8,14-triazatetracyclo[$10.3.1.0^{2,11}.0^{4,9}$]-hexadeca-2(11),3,5,7,9-pentaene in solution phase with a solution of succinic acid. Preferably, the contacting step is carried out over a period of between 1 and 24 hours, more preferably between 5 and 15 hours, and comprising stirring or mixing the resulting mixture. A preferred embodiment of the process is wherein step (i) is run between ambient temperature and the refluxing temperature of the solvent; more preferably, between ambient temperature and the refluxing temperature of 2-propanol, i.e., about 80° C.; most preferably, the process in run between 30 and 60° C.

DETAILED DESCRIPTION OF THE INVENTION

The compound, 5,8,14-triazatetracyclo[$10.3.1.0^{2,11}.0^{4,9}$]-hexadeca-2(11),3,5,7,9-pentaene is a nicotinic partial agonist for the treatment of a number of CNS diseases, disorders and conditions including, in particular, nicotine dependency, addiction and withdrawal. The succinate salts of 5,8,14-triazatetracyclo[$10.3.1.0^{2,11}.0^{4,9}$]-hexadeca-2(11),3,5,7,9-pentaene are only slightly hygroscopic and have high aqueous solubility. These characteristics make the succinate salt highly suitable for pharmaceutical formulation use.

Although in general the acid addition salts of 5,8,14-triazatetracyclo[$10.3.1.0^{2,11}.0^{4,9}$]-hexadeca-2(11),3,5,7,9-pentaene are all crystalline, the majority of those salts are so hygroscopic as to render them poor candidates for pharmaceutical formulation use. The anhydrous succinate salt of the present invention exhibits a hygroscopicity of approximately 1.97% wt/wt on exposure to 90% relative humidity in a moisture chamber. The aqueous solubility of the anhydrous succinate salt is 442 mg/ml. Further, the anhydrous succinate salt of 5,8,14-triazatetracyclo[$10.3.1.0^{2,11}.0^{4,9}$]-hexadeca-2(11),3,5,7,9-pentaene exhibits excellent solid state stability both in light and elevated temperatures as well as high humidity challenges.

The aqueous solubility of the anhydrous succinate salt has been measured under various conditions: >10 mg/mL in pH 4 buffer; >10 mg/mL in pH 10 buffer; >10 mg/mL in 0.1 N HCl; and >10 mg/mL in 0.1 N NaOH. The solubility of the anhydrous succinate salt has also been measured in various solvents: >10 mg/mL in methanol; 0.1 mg/mL in acetonitrile and <0.01 mg/mL in hexane. The hygroscopicity of the anhydrous succinate salt has also been measured under various conditions: 0.0% moisture gain at 20% Relative Humidity; 0.3% moisture gain at 40% Relative Humidity; 0.6% moisture gain at 60% Relative Humidity; 0.9% moisture gain at 80% Relative Humidity and 1.3% moisture gain at 95% Relative Humidity.

The anhydrous succinate salt has been prepared under different conditions via dissolving 5,8,14-triazatetracyclo [$10.3.1.0^{2,11}.0^{4,9}$]-hexadeca-2(11),3,5,7,9-pentaene in acetone or 2-propanol and then added to a succinic acid solution also in acetone. A slurry is formed and allowed to stir at 20 to 25° C. for approximately 24 hours. The product crystallizes on agitation to give the desired anhydrous salt usually in high yield. The product crystals are small and generally agglomerated or aggregated together. The hydrate salt can be formed via the use of a water containing solvents, i.e., 50:50 mixtures of acetone or 2-propanol.

Differential Scanning Calorimetry

Figure 2:
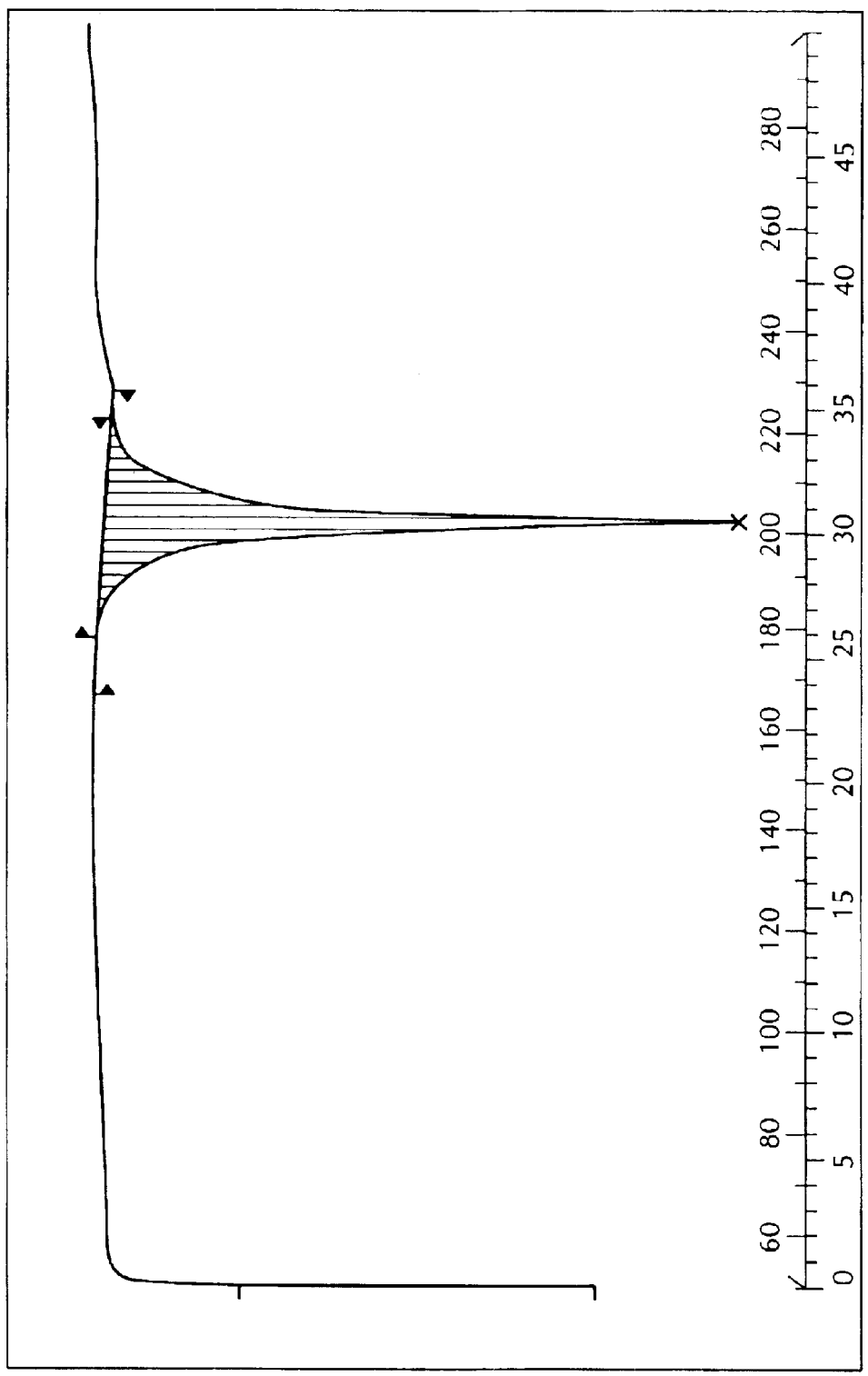
FIG. 2 is the differential scanning calorimetric trace of the anhydrous succinate salt of 5,8,14-triazatetracyclo [10.3.1.0$^{2,11}$.0$^{4,9}$]-hexadeca-2(11),3,5,7,9-pentaene.

The solid state thermal behavior of the succinate salt of the invention was investigated by differential scanning calorimetry (DSC). The trace for the anhydrous succinate salt is shown in FIG. 2; the hydrate succinate salt in FIG. 4. The DSC thermogram was obtained on a Mettler Toledo DSC 821$^e$ (STAR$^e$ System). Generally, samples between 1 and 10 mg were prepared in crimped aluminum pans with a small pinhole. The measurements were run at a heating rate of 5° C. per minute in the range of 30 to 300° C.

Figure 4:
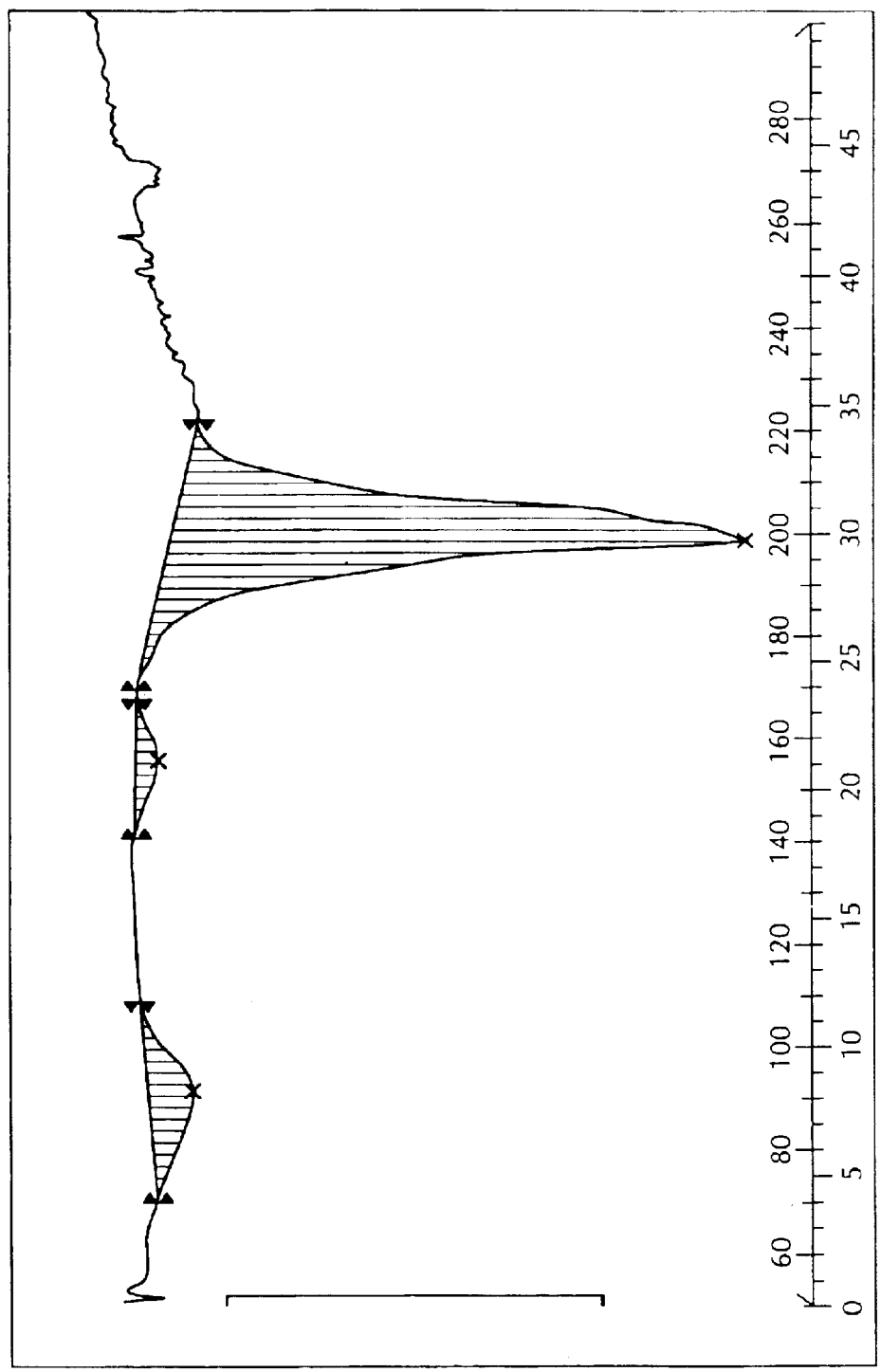
FIG. 4 is the differential scanning calorimetric trace of the succinate salt hydrate of 5,8,14-triazatetracyclo[10. 3.1.0$^{2,11}$.0$^{4,9}$]-hexadeca-2(11),3,5,7,9-pentaene.

As seen in FIG. 2, the anhydrous succinate salt exhibits onset of melt transition at about 198° C. (more precisely measured at 197.8° C.). As seen in FIG. 4, the succinate salt hydrate exhibits tow solid—solid transitions with onsets at about 70° C. and about 144° C., and an onset of melt transition at about 191° C. (more precisely measured at 190.9° C.). One of skill in the art will however note that in DSC measurement there is a certain degree of variability in actual measured onset and peak temperatures which occur depending on rate of heating, crystal shape and purity, and other measurement parameters. Further, the anhydrous succinate salt is characterized in that it forms prism-shaped crystals and has an onset of melting transition point at about 198° C. as measured by differential scanning calorimetry (DSC). Further, the anhydrous succinate salt of the invention is also characterized in having an aqueous solubility of 442 mg/ml and a native pH of 4.7 in aqueous solution. In addition, the anhydrous succinate salt has a hygroscopicity of approximately 1.97% at 90% relative humidity.

Powder X-ray Diffraction Patterns

The power x-ray diffraction patterns for the succinate salt of the invention was collected using a Bruker D5000 diffractometer (Bruker AXS, Madison, Wis.) equipped with copper radiation $CuK_\alpha$, fixed slits (1.0, 1.0, 0.6 mm), and a Kevex solid state detector. Data was collected from 3.0 to 40.0 degrees in two theta (2θ) using a step size of 0.04 degrees and a step time of 1.0 seconds.

The x-ray powder diffraction pattern of the succinate salts were conducted with a copper anode with wavelength 1 at 1.54056 and wavelength 2 at 1.54439 (relative intensity: 0.500). The range for 2θ was between 3.0 to 40.0 degrees with a step size of 0.04 degrees, a step time of 1.00 second, a smoothing width of 0.300 and a threshold of 1.0.

The diffraction peaks at diffraction angles (2θ) in the measured powder X-ray diffraction analysis for the anhydrous succinate salt are shown in Table I. The relative intensities, however, may change depending on the crystal size and morphology. The actual measured powder diffractogram is displayed in FIG. 1.

TABLE I

Powder X-ray Diffraction Pattern for with Intensities and Peak Locations of Diffraction Lines.

| Angle 2θ | d-value (Å) | I (rel.) |
|---|---|---|
| 6.5 | 13.5 | 38% |
| 13.1 | 6.7 | 100 |
| 16.5 | 5.4 | 49 |
| 17.0 | 5.2 | 78 |
| 19.8 | 4.5 | 63 |
| 22.2 | 4.0 | 79 |
| 23.8 | 3.7 | 77 |

Table II sets forth the 2θ and the d-spacings for the highest relative intensities for the powder x-ray diffraction pattern.

TABLE II

Powder X-ray Diffraction Intensities and Peak Locations for Anhydrous Succinate Salt.

| Angle 2θ | d-value (Å) | I (rel.) |
|---|---|---|
| 13.1 | 6.7 | 100 |
| 17.0 | 5.2 | 78 |
| 22.2 | 4.0 | 79 |
| 23.8 | 3.7 | 77 |

Figure 3:
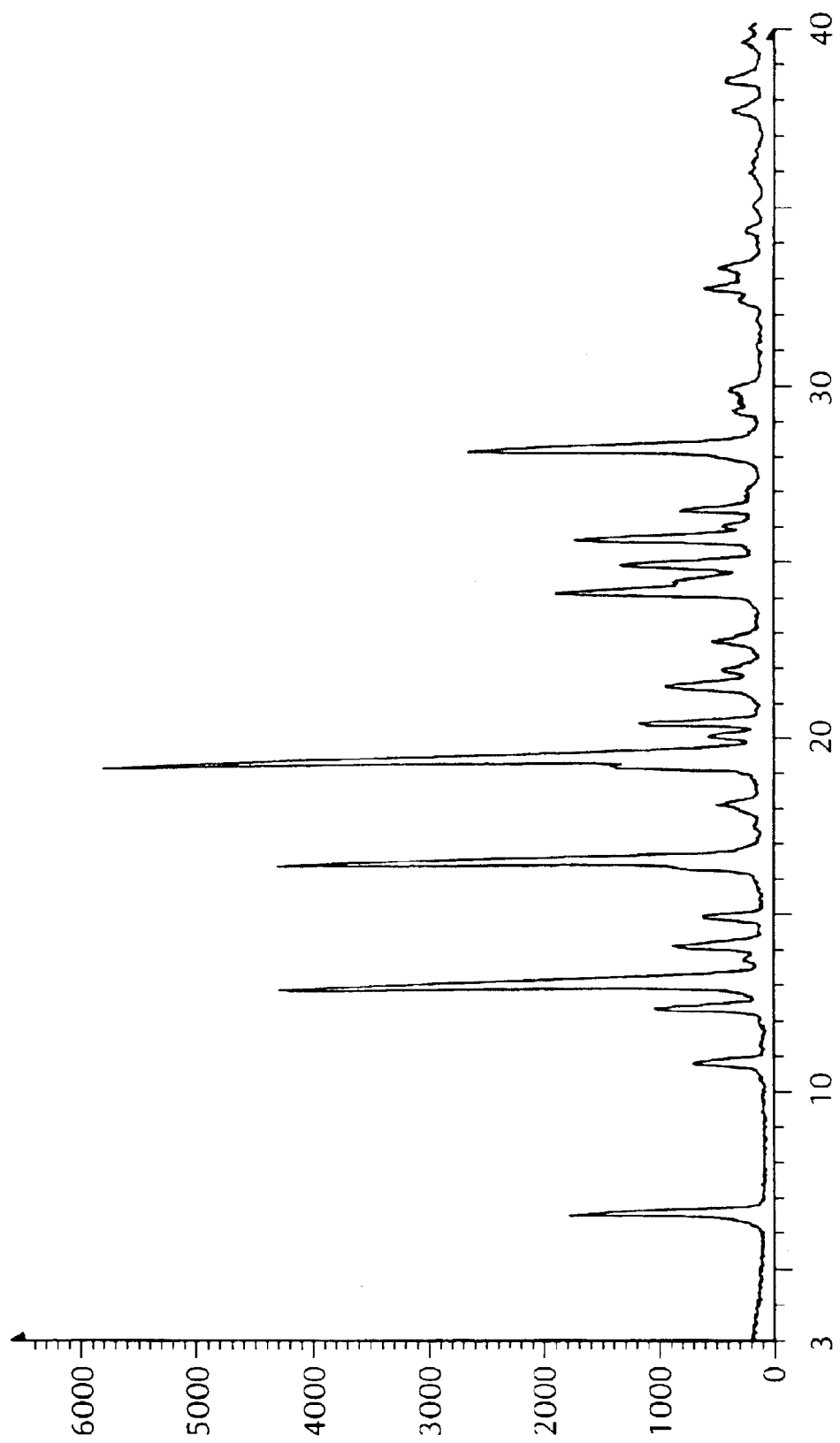
FIG. 3 is the observed powder X-ray diffraction pattern of the succinate salt hydrate of 5,8,14-triazatetracyclo [10.3.1.0$^{2,11}$.0$^{4,9}$]-hexadeca-2(11),3,5,7,9-pentaene (y axis is linear counts per second; X in degrees 2 theta).

The diffraction peaks at diffraction angles (2θ) in the measured powder X-ray diffraction analysis for the succinate salt hydrate are shown in Table III. The relative intensities, however, may change depending on the crystal size and morphology. The actual measured powder diffractogram is displayed in FIG. 3.

TABLE III

Powder X-ray Diffraction Pattern for with Intensities and Peak Locations of Diffraction Lines for the Succinate Salt Hydrate.

| Angle 2θ | d-value (Å) | I (rel.) |
|---|---|---|
| 6.5 | 13.6 | 30% |
| 13.0 | 6.8 | 73 |
| 16.5 | 5.4 | 74 |
| 19.4 | 4.6 | 100 |
| 24.2 | 3.7 | 32 |
| 28.3 | 3.2 | 45 |

Table IV sets forth the 2θ and the d-spacings for the highest relative intensities for the powder x-ray diffraction pattern of the hydrate succinate salt.

TABLE IV

Powder X-ray Diffraction Intensities and Peak Locations for the Succinate Salt Hydrate.

| Angle 2θ | d-value (Å) | I (rel.) |
|---|---|---|
| 13.0 | 6.8 | 73 |
| 16.5 | 5.4 | 74 |
| 19.4 | 4.6 | 100 |

The succinate salts of the invention (hereafter "the active salts") can be administered via either the oral, transdermal (e.g., through the use of a patch), intranasal, sublingual, rectal, parenteral or topical routes. Transdermal and oral administration are preferred. An active salt can, most desirably, administered in dosages ranging from about 0.01 mg up to about 1500 mg per day, preferably from about 0.1 to about 300 mg per day in single or divided doses, although variations will necessarily occur depending upon the weight and condition of the subject being treated and the particular route of administration chosen. However, a dosage level that is in the range of about 0.001 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

An active salt can be administered alone or in combination with pharmaceutically acceptable carriers or diluents by any of the several routes previously indicated. More particularly, an active salt can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, an active salt is present in such dosage forms at concentration levels ranging from about 5.0% to about 70% by weight.

For oral administration, tablets containing various excipients such as microcrystalline cellulose, sodium succinate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of a similar type may also be employed as fillers in gelatin capsules; preferred materials in this connection also include lactose or milk sugar, as well as high molecular weight polyethylene glycols. When aqueous suspensions and/or elixirs are desired for oral administration the active ingredient may be combined with various sweetening or flavoring agents, coloring matter and, if so desired, emulsifying and/or suspending agents, together with such diluents as water, ethanol, propylene glycol, glycerin and various combinations thereof.

For parenteral administration, a solution of an active salt in either sesame or peanut oil or in aqueous propylene glycol can be employed. The aqueous solutions should be suitably buffered (preferably pH greater than 8), if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer an active salt topically and this can be done by way of creams, a patch, jellies, gels, pastes, ointments and the like, in accordance with standard pharmaceutical practice.

The following example illustrates the methods and compounds of the present invention. It will be understood, however, that the invention is not limited to the specific Examples.

EXAMPLE 1

Anhydrous Succinate Salt of 5,8,14-Triazatetracyclo[10.3.1.0$^{2,11}$.0$^{4,9}$]-hexadeca-2(11),3,5,7,9-pentaene

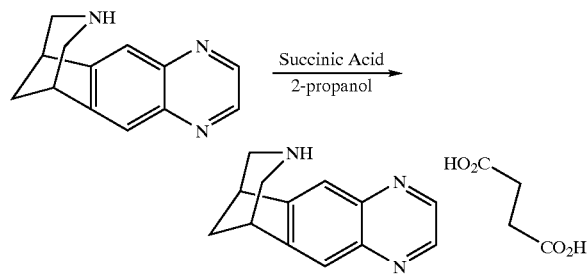

A 200 ml reactor was charged with the free base 5,8,14-triazatetracyclo[10.3.1.0$^{2,11}$.0$^{4,9}$]-hexadeca-2(11),3,5,7,9-pentaene (9 g; 0.047 mol) and 2-propanol (90 ml, 10 ml/g). The mixture was warmed to 50 to 55° C. to give a solution. The mixture was filtered to remove any specks and fibers present. The clarified solution (at 50 to 55° C.) was treated with a clarified solution of succinic acid (7.1 g., 0.0598 mol, 1.4 equiv.) dissolved in 2-propanol (36 ml) over about 5 to 15 minutes. The mixture was stirred at 50 to 55° C. for about 1 hour allowing crystallization to occur. The crystal slurry was cooled to 0 to 5° C. over about 1 hour and the final slurry was stirred for about 1 hour. The product was isolated by filtration, washed with 2-propanol (18 ml) and dried at 20 to 30° C. under vacuum for about 24 hours.

EXAMPLE 2

Succinate Salt Hydrate of 5,8,14-Triazatetracyclo[10.3.1.0$^{2,11}$.0$^{4,9}$]-hexadeca-2(11),3,5,7,9-pentaene A reactor was charged with the anhydrous succinate salt prepared in Example 1 and water (500 mL). The suspension was stirred at about 40 C for about 12 hours. The crystalline product was filtered and dried in vacuum to afford the succinate hydrate salt.

What is claimed is:

1. A succinate salt of 5,8,14-triazatetracyclo[10.3.1.0$^{2,11}$.0$^{4,9}$]-hexadeca-2(11),3,5,7,9-pentaene.

2. The compound according to claim 1 wherein the salt is anhydrous.

3. A compound according to claim 2 having an x-ray diffraction pattern characterized substantially by an x-ray diffraction pattern peaks as measured with copper radiation of a 2θ of about 13.3 and 17.2.

4. A compound according to claim 2 having an x-ray diffraction pattern characterized substantially by the following principal x-ray diffraction pattern peaks expressed in terms of 2θ and d-spacings as measured with copper radiation:

| Angle 2θ | d-value (Å) |
| --- | --- |
| 13.1 | 6.7 |
| 17.0 | 5.2 |
| 22.2 | 4.0 |
| 23.8 | 3.7 |

5. A compound according to claim 2 characterized by an onset of melting/decomposition transition at about 198° C.

6. A pharmaceutical composition comprising a compound according to claim 2 and a pharmaceutically acceptable carrier.

7. A compound according to claim 1 wherein the salt is a hydrate.

8. A compound according to claim 7 having an x-ray diffraction pattern characterized substantially by the following principal x-ray diffraction pattern peaks expressed in terms of 2θ and d-spacings as measured with copper radiation:

| Angle 2θ | d-value (Å) |
| --- | --- |
| 13.0 | 6.8 |
| 16.5 | 5.4 |
| 19.4 | 4.6 |

9. A compound according to claim 7 characterized by an onset of melting/decomposition transition at about 198° C.

10. A pharmaceutical composition comprising a compound according to claim 7 and a pharmaceutically acceptable carrier.

11. A method of treatment for nicotine dependency, addiction or withdrawal in a mammal comprising the administration of a compound according to any of claim 1 to a subject in need thereof.

12. A process for the preparation of the anhydrous succinate salt of 5,8,12-triazatetracyclo[10.3.1.0$^{2,11}$.0$^{4,9}$]- hexadeca-2(11),3,5,7,9-pentaene according to claim 2 comprising the steps of (i) contacting 5,8,14-triazatetracyclo[10.3.1.0$^{2,11}$.0$^{4,9}$]-hexadeca-2(11),3,5,7,9-pentaene in a suitable solvent with succinic acid; and (ii) collecting the crystals formed.

13. A process according to claim 12 wherein the suitable solvent is selected from the group consisting of a ($C_1$–$C_6$) alkyl alcohol, ($C_1$–$C_6$)alkyl ketone and ($C_1$–$C_6$)alkyl ether.

14. A process according to claim 12 wherein the suitable solvent is acetone or 2-propanol.

15. A process according to claim 12 wherein the contacting of step (i) is carried out by contacting 5,8,14-triazatetracyclo[10.3.1.0$^{2,11}$.0$^{4,9}$]-hexadeca-2(11),3,5,7,9-pentaene in solution phase with a solution of succinic acid.

16. A process according to claim 12 wherein the contacting step is carried out over a period of between 1 and 24 hours.

17. A process for the preparation of the succinate salt hydrate of 5,8,14-triazatetracyclo[10.3.1.0$^{2,11}$.0$^{4,9}$]-hexadeca-2(11),3,5,7,9-pentaene according to claim 7 comprising the steps of (i) contacting 5,8,14-triazatetracyclo[10.3.1.0$^{2,11}$.0$^{4,9}$]-hexadeca-2(11),3,5,7,9-pentaene in a suitable solvent with succinic acid; and (ii) collecting the crystals formed.

18. A process according to claim 17 wherein the suitable solvent is a mixture of 2-propanol or acetone and water.

* * * * *